(12) United States Patent
Hallinan et al.

(10) Patent No.: US 8,309,761 B2
(45) Date of Patent: Nov. 13, 2012

(54) REMOVING HYDROCARBON IMPURITIES FROM ACETIC ACID BY IONIC LIQUID EXTRACTION

(75) Inventors: Noel C. Hallinan, Loveland, OH (US); Brian A. Salisbury, Oxford, PA (US)

(73) Assignee: Lyondell Chemical Technology, L.P., Houston, TX (US)

( * ) Notice: Subject to any disclaimer, the term of this patent is extended or adjusted under 35 U.S.C. 154(b) by 102 days.

(21) Appl. No.: 12/807,110

(22) Filed: Aug. 27, 2010

(65) Prior Publication Data

US 2011/0004015 A1 Jan. 6, 2011

Related U.S. Application Data

(62) Division of application No. 12/151,554, filed on May 7, 2008, now Pat. No. 7,812,191.

(51) Int. Cl.
*C07C 53/00* (2006.01)
(52) U.S. Cl. ..................................................... 562/512
(58) Field of Classification Search .................. 562/512
See application file for complete search history.

(56) References Cited

U.S. PATENT DOCUMENTS

| 4,102,922 A | 7/1978 | Price |
| 5,817,869 A | 10/1998 | Hinnenkamp et al. |
| 5,932,764 A | 8/1999 | Morris et al. |
| 7,812,191 B2 * | 10/2010 | Hallinan et al. ............... 562/512 |
| 2007/0193952 A1 | 8/2007 | Maase et al. |

FOREIGN PATENT DOCUMENTS

| CN | 101 117 327 A | 2/2008 |
| GB | 2418926 | 4/2006 |
| WO | WO 2008/024198 | 2/2008 |

OTHER PUBLICATIONS

Matsumoto M. et al.: *Extraction of organic acids using imidazolium-based ionic liquids and their toxicity to Lactobacillus rhamnosus*, Separation and Purification Technology, Elsevier Science, Amsterdam, NL, vol. 40, No. 1, Nov. 15, 2004, pp. 97-101, XP004558244, ISSN: 1383-5866, Figure 1; Table 1.

Huddleston. J.G. et al.: *Characterization and Comparison of Hydrophilic and Hydrophobic Room Temperature Ionic Liquids Incorporating the Imidazolium Cation*, Green Chemistry, Royal Society of Chemistry, Cambridge, GB, vol. 3, No. 4, Jan. 1, 2001, pp. 156-164, XP009073032, ISSN: 1463-9262, pp. 157-158, Table 2.

\* cited by examiner

*Primary Examiner* — Rei-tsang Shiao

(57) ABSTRACT

A method for removing hydrocarbon impurities from acetic acid is disclosed. The method comprises extracting acetic acid with a hydrophilic imidazolium salt. The imidazolium salt preferably has the general structure of

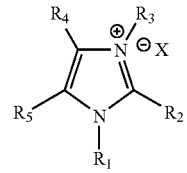

wherein $X^{\ominus}$ is a counter ion and $R_1$, $R_2$, $R_3$, $R_4$, and $R_5$ are independently selected from the group consisting of $C_1$-$C_6$ hydrocarbon substitutes. The method is useful for removing hydrocarbon impurities from the alkane distillation bottoms stream of a methanol carbonylation process.

8 Claims, No Drawings

REMOVING HYDROCARBON IMPURITIES FROM ACETIC ACID BY IONIC LIQUID EXTRACTION

Division of application Ser. No. 12/151,554, filed May 7, 2008 now U.S. Pat. No. 7,812,191.

FIELD OF THE INVENTION

The invention relates to the preparation of acetic acid. More particularly, the invention relates to a method for removing hydrocarbon impurities from acetic acid by ionic liquid extraction.

BACKGROUND OF THE INVENTION

The carbonylation of methanol produces acetic acid:

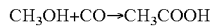

Prior to 1970, acetic acid was made using a cobalt catalyst. A rhodium carbonyl iodide catalyst was developed in 1970 by Monsanto. The rhodium catalyst is considerably more active than the cobalt catalyst, which allows lower reaction pressure and temperature. Most importantly, the rhodium catalyst gives high selectivity to acetic acid.

One problem associated with the original Monsanto process is that a large amount of water (about 14%) is needed to produce hydrogen in the reactor via the water-gas shift reaction ($CO+H_2O \rightleftharpoons CO_2+H_2$). Water and hydrogen are needed to react with precipitated Rh(III) and inactive $[Rh_2(CO)_4]^-$ to regenerate the active Rh(I) catalyst. This large amount of water increases the amount of hydrogen iodide, which is highly corrosive and leads to engineering problems. Further, removing a large amount of water from the acetic acid product is costly.

In the late '70s Celanese modified the carbonylation process by adding lithium iodide salt to the carbonylation. Lithium iodide salt increases the catalyst stability by minimizing the side reactions that produce inactive Rh(III) species and therefore the amount of water needed is reduced. However, the high concentration of lithium iodide salt promotes stress crack corrosion of the reactor vessels. Furthermore, the use of iodide salts increases the iodide impurities in the acetic acid product.

In the early '90s, Millennium Petrochemicals developed a new rhodium carbonylation catalyst system that does not use iodide salt. The catalyst system uses a pentavalent Group VA oxide such as triphenylphosphine oxide as a catalyst stabilizer. The Millennium catalyst system not only reduces the amount of water needed but also increases the carbonylation rate and acetic acid yield. See U.S. Pat. No. 5,817,869.

One challenge still facing the industry is that lowering water concentration in the methanol carbonylation increases the formation of hydrocarbon impurities such as alkanes and aromatics. Methods for removing alkanes from acetic acid are known. For instance, U.S. Pat. No. 4,102,922 discloses an alkane removal method. According to the '922 patent, a slip stream from the heavy phase which comprises methyl iodide, acetic acid, water and alkanes is fed to an alkane distillation column with an overhead temperature of about 75° C. and a bottoms temperature of about 142° C. The bottoms temperature is run significantly higher than the overhead in order to minimize methyl iodide loss to the bottoms stream. The overhead of the alkane distillation, comprising mainly methyl iodide, is recycled to the reaction section. The bottoms stream comprising about 50% acetic acid and about 40% alkanes is removed from the system as waste. One problem associated with this method is that due to the high bottoms temperature, low boiling alkanes such as 2-methylpentane come with the overhead methyl iodide. This results in a build up of the low boiling alkanes in the reaction system as the overhead methyl iodide is recycled into the carbonylation reaction.

A new method for removing alkanes and other hydrocarbon impurities from the acetic acid production process is needed. Ideally, the method can effectively remove both high boiling and low boiling hydrocarbon impurities from the acetic acid production process.

SUMMARY OF THE INVENTION

The invention is a method for removing hydrocarbon impurities from acetic acid. The method comprises extracting acetic acid with an ionic liquid. Suitable ionic liquids are hydrophilic imidazolium salts. By hydrophilic imidazolium salts, we mean any imidazolium salts which can cause phase separation between acetic acid and the hydrocarbon impurities. Preferably, the imidazolium salts have the general structure:

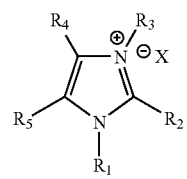

wherein $X^{\ominus}$ is a counter ion and $R_1$, $R_2$, $R_3$, $R_4$, and $R_5$ are independently selected from the group consisting of hydrogen and $C_1$-$C_6$ hydrocarbon substituents. The method can be used for removing hydrocarbon impurities from acetic acid product. More importantly, the method can be used to remove hydrocarbon impurities from the alkanes distillation column bottoms stream of acetic acid production.

DETAILED DESCRIPTION OF THE INVENTION

Ionic liquids suitable for the use in the invention are hydrophilic imidazolium salts which can cause phase separation between acetic acid and hydrocarbon impurities. Preferably, the imidazolium salts have the general structure:

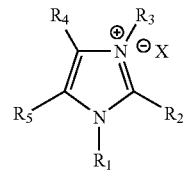

wherein $X^{\ominus}$ is a counter ion and $R_1$, $R_2$, $R_3$, $R_4$, and $R_5$ are independently selected from the group consisting of hydrogen and $C_1$-$C_6$ hydrocarbon substituents. Preferably $X^{\ominus}$ is a halide. More preferably $X^{\ominus}$ is an iodide or chloride. Preferably, $R_1$, $R_2$, $R_3$, $R_4$, and $R_5$ are independently selected from $C_1$-$C_4$ hydrocarbon substituents. Examples of ionic liquids suitable for the use in the invention include 1-butyl-3-methylimidazolium iodide, 1-butyl-2,3-dimethylimidazolium iodide, 1-butyl-2,3-dimethylimidazolium chloride, the like, and mixtures thereof.

Hydrocarbon impurities are produced by the side reactions of methanol carbonylation. Examples of hydrocarbon impurities include alkanes, alkenes, and aromatics. Alkane impurities commonly seen in the methanol carbonylation are $C_3$-$C_{12}$ alkanes including propane, butane, pentane, 2-methylbutane, 2,3-dimethylbutane, 2-methyl pentane, 3-methylpentane, hexane, octane, decane, cyclohexane, the like, and mixtures thereof. Commonly seen alkenes include propylene, butene, octene, the like, and mixtures thereof. Commonly seen aromatics include benzene, n-propylbenzene, toluene, xylene, the like, and mixtures thereof.

The extraction is performed by mixing an ionic liquid with acetic acid and causing phase separation. The light phase comprises the hydrocarbon impurities and the heavy phase comprises acetic acid and the ionic liquid. One advantage of the invention is that the light phase contains essentially no ionic liquid so that it can be easily disposed of without further separation. Another advantage of the invention is that acetic acid and the ionic liquid in the heavy phase can be easily separated because the ionic liquid has a much higher boiling point than acetic acid. A purer acetic acid product can be thus produced by distillation of the heavy phase and the ionic liquid can be recovered and reused. Typically, the ratio of ionic liquid to acetic acid is from 10/90 to 90/10, preferably, from 50/50 to 90/10 (V/V). The extraction is preferably performed at an ambient temperature.

The method of the invention can be used effectively to remove hydrocarbon impurities from the alkane distillation bottoms stream of methanol carbonylation process. The alkane distillation bottoms stream comprises, in addition to acetic acid, methyl iodide.

The carbonylation reaction is usually performed in the presence of a carbonylation catalyst and a catalyst stabilizer. Suitable carbonylation catalysts include those known in the acetic acid industry. Examples of suitable carbonylation catalysts include rhodium catalysts and iridium catalysts.

Suitable rhodium catalysts are taught, for example, by U.S. Pat. No. 5,817,869. Suitable rhodium catalysts include rhodium metal and rhodium compounds. Preferably, the rhodium compounds are selected from the group consisting of rhodium salts, rhodium oxides, rhodium acetates, organo-rhodium compounds, coordination compounds of rhodium, the like, and mixtures thereof. More preferably, the rhodium compounds are selected from the group consisting of $Rh_2(CO)_4I_2$, $Rh_2(CO)_4Br_2$, $Rh_2(CO)_4Cl_2$, $Rh(CH_3CO_2)_2$, $Rh(CH_3CO_2)_3$, $[H]Rh(CO)_2I_2$, the like, and mixtures thereof. Most preferably, the rhodium compounds are selected from the group consisting of $[H]Rh(CO)_2I_2$, $Rh(CH_3CO_2)_2$, the like, and mixtures thereof.

Suitable iridium catalysts are taught, for example, by U.S. Pat. No. 5,932,764. Suitable iridium catalysts include iridium metal and iridium compounds. Examples of suitable iridium compounds include $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_4I_2]^-H^+$, $[Ir(CO)_2Br_2]^-H^+$, $[Ir(CO)_2I_2]^-H^+$, $[Ir(CH_3)I_3(CO)_2]^-H^+$, $Ir_4(CO)_{12}$, $IrCl_3 \cdot 4H_2O$, $IrBr_3 \cdot 4H_2O$, $Ir_3(CO)_{12}$, $Ir_2O_3$, $IrO_2$, $Ir(acac)(CO)_2$, $Ir(acac)_3$, $Ir(OAc)_3$, $[Ir_3O(OAc)_6(H_2O)_3][OAc]$, and $H_2[IrCl_6]$. Preferably, the iridium compounds are selected from the group consisting of acetates, oxalates, acetoacetates, the like, and mixtures thereof. More preferably, the iridium compounds are acetates.

The iridium catalyst is preferably used with a co-catalyst. Preferred co-catalysts include metals and metal compounds selected from the group consisting of osmium, rhenium, ruthenium, cadmium, mercury, zinc, gallium, indium, and tungsten, their compounds, the like, and mixtures thereof. More preferred co-catalysts are selected from the group consisting of ruthenium compounds and osmium compounds. Most preferred co-catalysts are ruthenium compounds. Preferably, the co-catalysts are acetates.

The carbonylation reaction is preferably performed in the presence of a catalyst stabilizer. Suitable catalyst stabilizers include those known to the industry. In general, there are two types of catalyst stabilizers. The first type of catalyst stabilizer is metal iodide salt such as lithium iodide. The second type of catalyst stabilizer is a non-salt stabilizer. Preferred non-salt stabilizers are pentavalent Group VA oxides. See U.S. Pat. No. 5,817,869. Phosphine oxides are more preferred. Triphenylphosphine oxides are most preferred.

The carbonylation reaction is preferably performed in the presence of water. Preferably, the concentration of water present is from about 2 wt % to about 14 wt % based on the total weight of the reaction medium. More preferably, the water concentration is from about 2 wt % to about 10 wt %. Most preferably, the water concentration is from about 4 wt % to about 8 wt %.

The reaction is preferably performed in the presence of methyl acetate. Methyl acetate can be formed in situ. If desirable, methyl acetate can be added as a starting material to the reaction mixture. Preferably, the concentration of methyl acetate is from about 2 wt % to about 20 wt % based on the total weight of the reaction medium. More preferably, the concentration of methyl acetate is from about 2 wt % to about 16 wt %. Most preferably, the concentration of methyl acetate is from about 2 wt % to about 8 wt %. Alternatively, methyl acetate or a mixture of methyl acetate and methanol from byproduct streams of the hydroysis/methanolysis of polyvinyl acetate can be used for the carbonylation reaction.

The reaction is usually performed in the presence of methyl iodide. Methyl iodide is a catalyst promoter. Preferably, the concentration of methyl iodide is from about 0.6 wt % to about 36 wt % based on the total weight of the reaction medium. More preferably, the concentration of methyl iodide is from about 4 wt % to about 24 wt %. Most preferably, the concentration of methyl iodide is from about 6 wt % to about 20 wt %. Alternatively, methyl iodide can be generated in the carbonylation reactor by adding hydrogen iodide (HI).

Hydrogen may also be fed into the reactor. Addition of hydrogen can enhance the carbonylation efficiency. Preferably, the concentration of hydrogen is from about 0.1 mol % to about 5 mol % of carbon monoxide in the reactor. More preferably, the concentration of hydrogen is from about 0.3 mol % to about 3 mol % of carbon monoxide in the reactor.

Methanol and carbon monoxide are fed to the carbonylation reactor. The methanol feed to the carbonylation reaction can come from a syngas-methanol facility or any other source. Methanol does not react directly with carbon monoxide to form acetic acid. It is converted to methyl iodide by the hydrogen iodide present in the reactor and then reacts with carbon monoxide and water to give acetic acid and regenerate hydrogen iodide. Carbon monoxide not only becomes part of the acetic acid molecule, but it also plays an important role in the formation and stability of the active catalyst.

The carbonylation reaction is preferably performed at a temperature within the range of about 150° C. to about 250° C. More preferably, the reaction is performed at a temperature within the range of about 150° C. to about 200° C. The carbonylation reaction is preferably performed under a pressure within the range of about 200 psig to about 2,000 psig. More preferably, the reaction is performed under a pressure within the range of about 300 psig to about 500 psig.

An acetic acid product stream is withdrawn from the reactor and is separated, by a flash separation, into a liquid fraction comprising the catalyst and the catalyst stabilizer and a vapor fraction comprising the acetic acid product, the reactants, water, methyl iodide, and impurities generated during the carbonylation reaction including alkanes, alkenes, and aromatics. The liquid fraction is recycled to the carbonylation reactor. The vapor fraction is then passed to a distillation column.

The distillation column, the so-called "light ends distillation," separates an overhead comprising methyl iodide, water, methanol, methyl acetate, and the hydrocarbon impurities from an acetic acid stream comprising acetic acid, a small amount of water, and some heavy impurities such as propionic acid. The acetic acid stream may be passed to a drying column to remove water and then be subjected to distillation, the so-called "heavy ends distillation," to remove the heavy impurities.

The overhead stream from the light ends distillation usually comprises from about 60 wt % to about 90 wt % of methyl iodide, from about 5 wt % to about 15 wt % of methyl acetate, from about 1 wt % to about 10 wt % of acetic acid, 1 wt % or less of water, from about 1 wt % to about 10 wt % of hydrocarbon impurities, and about 2 wt % or less of aldehyde impurities based on the total weight of the overhead.

The overhead stream is condensed and separated in a decanter to a light, aqueous phase and a heavy, organic phase. The heavy, organic phase comprises predominantly methyl iodide (greater than 50%) and the hydrocarbon impurities. The light, aqueous phase comprises predominantly water (greater than 50%), acetic acid, and methyl acetate. The aqueous phase is usually recycled to the reactor or to the light ends distillation.

At least a portion of the heavy, organic phase is distilled to form a vapor stream comprising the majority of methyl iodide (over 50% of the methyl iodide from the heavy organic phase) and a bottoms stream comprising the majority of acetic acid, methyl acetate, methyl iodide, and the hydrocarbon impurities (over 50% of each component from the heavy organic phase). The overhead temperature of the distillation is preferably below about 75° C. so that there is no significant amount of hydrocarbon impurities coming out with the vapor stream. More preferably, the overhead temperature of the distillation is within the range of about 43° C. (boiling point of methyl iodide) to about 75° C. Most preferably, the overhead temperature of the distillation is within the range of about 43° C. to about 60° C. The particularly preferred overhead temperature of the distillation is within the range of about 43° C. to about 45° C. The closer the overhead temperature of the distillation to the boiling point of methyl iodide, the less the amount of hydrocarbon impurities existing in the vapor stream. The vapor stream is recycled to the carbonylation reaction. Lowering the overhead temperature of the heavy phase distillation, although reducing the hydrocarbon impurities in the vapor stream, results in a higher concentration of methyl iodide in the bottoms stream. According to current industrial practice, the bottoms stream is disposed as waste. Thus, an increased amount of methyl iodide, an expensive material, is wasted.

The bottoms stream is extracted with the ionic liquid to form a light phase comprising the majority of the hydrocarbon impurities and a heavy phase comprising the ionic liquid and the majority of water, acetic acid, and methyl iodide. The light phase is optionally disposed of and the heavy phase can be recycled to the carbonylation reaction. Alternatively, ionic liquid is removed from the heavy phase and the heavy phase is then recycled to the carbonylation reaction. Preferably, from about 5% to about 100% of the heavy, organic phase from the decanter is subjected to the distillation and extraction. More preferably, from about 5% to about 50% of the heavy, organic phase from the decanter is subjected to the distillation and extraction.

The ionic liquid to the bottoms stream of the alkanes distillation is preferably in the range of 90/10 to 10/90, more preferably from 75/25 to 25/75 (V/V). The bottoms stream of the alkanes distillation can be extracted more than once, if desired, by the ionic liquid.

The following examples are merely illustrative. Those skilled in the art will recognize many variations that are within the spirit of the invention and scope of the claims.

EXAMPLE 1

Extraction of Alkane Distillation Bottoms Stream with 1-butyl-3-methylimidazolium iodide (Ionic Liquid)

A simulated alkane distillation bottoms stream (7 parts by volume, containing 14.6 wt % of methyl iodide, 15.4 wt % of hexane, and 70 wt % of acetic acid) is mixed with 1-butyl-3-methylimidazolium iodide (7 parts by volume) in a vial at room temperature (25° C.). A phase separation occurs. The ratio of light phase to heavy phase is 0.109 by weight. The light phase and the heavy phase are analyzed by ATR (attenuated total reflectance) infrared probe measurements. The light phase contains 66 wt % of hexane, 14 wt % of methyl iodide, and 20 wt % of acetic acid. The heavy phase contains 56 wt % of ionic liquid, 6.5 wt % of methyl iodide, 36 wt % of acetic acid, and 1.5 wt % of hexane.

EXAMPLE 2

Extraction of Alkane Distillation Bottoms Stream with 1-butyl-3-methylimidazolium iodide Example 1 is repeated but the volume ratio of the ionic liquid to the simulated alkane distillation stream is 0.63. A phase separation occurs. The ratio of light phase to heavy phase is 0.180 by weight. The light phase contains 49 wt % of hexane, 16.3 wt % of methyl iodide, and 34.7 wt % of acetic acid. The heavy phase contains 44.6 wt % of ionic liquid, 7.8 wt % of methyl iodide, 45 wt % of acetic acid, and 2.6 wt % of hexane.

EXAMPLE 3

Extraction of Alkane Distillation Bottoms Stream with 1-butyl-3-methylimidazolium iodide Example 1 is repeated but the volume ratio of the ionic liquid to the simulated alkane distillation stream is 0.25. A phase separation occurs. The ratio of light phase to heavy phase is 0.541 by weight. The light phase contains 26.7 wt % of hexane, 13.3 wt % of methyl iodide, and 60 wt % of acetic acid. The heavy phase contains 30.4 wt % of ionic liquid, 10.9 wt % of methyl iodide, 54.1 wt % of acetic acid, and 4.6 wt % of hexane.

EXAMPLE 4

Extraction of Alkane Distillation Bottoms Stream with 1-butyl-3-methylimidazolium iodide Example 1 is repeated but the volume ratio of the ionic liquid to the simulated alkane distillation stream ratio is 0.15. A phase separation occurs. The ratio of light phase to heavy phase is 1.248 by weight. The light phase contains 19.7 wt % of hexane, 15 wt % of methyl iodide, and 65.3 wt % of acetic acid. The heavy phase contains 26.9 wt % of ionic liquid, 10.2 wt % of methyl iodide, 56.3 wt % of acetic acid, and 6.6 wt % of hexane.

TABLE 1

Summary of Examples 1-4

| Ex. No. | Ionic Liquid/Bottoms Stream Solution (V/V) | Light Phase/ Heavy Phase (W/W) | Light Phase composition, wt % | | | Heavy Phase Composition, wt % | | | Ionic Liquid |
|---|---|---|---|---|---|---|---|---|---|
| | | | Hexane | Mel | AcOH | Hexane | Mel | AcOH | |
| 1 | 1    | 0.109 | 66.6 | 14.2 | 19.2 | 1.5  | 6.5  | 36   | 56   |
| 2 | 0.63 | 0.180 | 49   | 16.3 | 34.7 | 2.6  | 7.8  | 45   | 44.6 |
| 3 | 0.25 | 0.541 | 26.7 | 13.3 | 60   | 4.6  | 10.9 | 54.1 | 30.4 |
| 4 | 0.15 | 1.248 | 19.7 | 15   | 65.3 | 6.6  | 10.2 | 56.3 | 26.9 |

EXAMPLES 5-8

Extraction of Alkane Distillation Bottoms Stream with 1-butyl-2,3-dimethylimidazolium chloride Example 1 is repeated but 1-butyl-2,3-dimethylimidazolium chloride is used as an ionic liquid and the ratio of ionic liquid to stimulated alkane distillation bottoms stream varies as indicated in Table 2. The results are listed in Table 2.

TABLE 2

Summary of Examples 5-8

| Ex. No. | Ionic Liquid/Bottoms Stream Solution (V/V) | Light Phase/ Heavy Phase (W/W) | Light Phase composition, wt % | | | Heavy Phase Composition, wt % | | | Ionic Liquid |
|---|---|---|---|---|---|---|---|---|---|
| | | | Hexane | Mel | AcOH | Hexane | Mel | AcOH | |
| 5 | 0.42 | 0.159 | 71.5 | 17.5 | 11.0 | 1.4  | 9.2  | 55.5 | 33.9 |
| 6 | 0.16 | 0.270 | 49.3 | 15.3 | 35.4 | 3.7  | 11.8 | 66.7 | 17.8 |
| 7 | 0.13 | 0.328 | 38.4 | 15.7 | 45.9 | 5.6  | 12.1 | 67.0 | 15.3 |
| 8 | 0.08 | 0.397 | 25.1 | 8.7  | 66.2 | 10.1 | 15.6 | 64.2 | 9.9  |

COMPARATIVE EXAMPLE 9

Extraction of Alkane Distillation Bottoms Stream with 1-butyl-2,3-dimethylimidazolium chloride Example 8 is repeated but the volume ratio of the ionic liquid to the stimulated alkane distillation bottoms stream is only 0.04. No phase separation is observed.

COMPARATIVE EXAMPLE 10

Extraction of Alkane Distillation Bottoms Stream with 1-dodecyl-3-methylimidazolium iodide Example 1 is repeated but the ionic liquid is 1-dodecyl-3-methylimidaolium iodide. No phase separation is observed.

COMPARATIVE EXAMPLE 11

Extraction of Alkane Distillation Bottoms Stream with trihexyl(tetradecyl)phosphonium chloride Example 1 is repeated but the ionic liquid is trihexyl(tetradecyl)phosphonium chloride. No phase separation is observed.

COMPARATIVE EXAMPLE 12

Extraction of Alkane Distillation Bottoms Stream with tetrabutylphosphonium chloride Example 1 is repeated but the ionic liquid is tetrabutylphosphonium chloride. No phase separation is observed.

We claim:
1. A method for removing a hydrocarbon impurity from an acetic acid production process, said method comprising:
 (a) reacting methanol and carbon monoxide in the presence of a carbonylation catalyst, a catalyst stabilizer, methyl iodide, water and methyl acetate to produce an acetic acid stream containing a hydrocarbon impurity;
 (b) flashing at least a portion of the acetic acid stream into a vapor stream comprising acetic acid, water, methanol, methyl acetate, methyl iodide and the hydrocarbon impurity, and a liquid stream comprising the catalyst and the catalyst stabilizer;

(c) separating the vapor stream from step (b) by distillation into a product stream comprising acetic acid and a minor amount of water, and an overhead stream comprising methyl iodide, water, methyl acetate, acetic acid and the hydrocarbon impurity;

(d) condensing and separating the overhead stream from step (c) into a light, aqueous phase comprising water, acetic acid, and methyl acetate, and a heavy, organic phase comprising methyl iodide, acetic acid, methyl acetate, and the hydrocarbon impurity; and (e) distilling at least a portion of the heavy, organic phase from step (d) into a vapor stream comprising methyl iodide and a bottoms stream comprising acetic acid, methyl acetate, methyl iodide, and the hydrocarbon impurity; and (f) extracting the bottoms stream of step (e) with an hydrophilic imidazolium salt, wherein the hydrophilic imidazolium salt has the general structure:

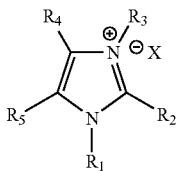

wherein $x^{\ominus}$ is a counter ion and $R_1$, $R_2$, $R_3$, $R_4$ and $R_5$ are independently selected from the consisting of hydrogen and $C_1$-$C_6$ hydrocarbon substitutes, and forming a light phase comprising the hydrocarbon impurity and a heavy phase comprising the ionic liquid, acetic acid, and methyl iodide.

2. The method of claim 1, which comprises removing the ionic liquid from the heavy phase from step (f) and then recycling the heavy phase to the carbonylation reaction of step (a).

3. The method of claim 1, wherein the catalyst is a rhodium catalyst.

4. The method of claim 1, wherein the catalyst stabilizer is triphenylphosphine oxide.

5. The method of claim 1, wherein the hydrocarbon impurity is selected from the group consisting of alkanes, alkenes, aromatics, and mixtures thereof.

6. The method of claim 1, the distillation of step (e) is conducted at an overhead temperature less than 75° C.

7. The method of claim 1, wherein the distillation of step (e) is conducted at an overhead temperature within the range of about 43° C. to about 60° C.

8. The method of claim 1, wherein the distillation of step (e) is conducted at an overhead temperature within the range of about 43° C. to about 45° C.

* * * * *